United States Patent [19]
De Lombaert

[11] Patent Number: 5,644,055
[45] Date of Patent: Jul. 1, 1997

[54] ANTIHYPERTENSIVE TRICYCLIC AZEPINE DERIVATIVES USEFUL AS INHIBITORS OF ENKEPHALINASE AND ACE

[75] Inventor: Stéphane De Lombaert, Bernardsville, N.J.

[73] Assignee: Ciba-Geigy Corporation, Tarrytown, N.Y.

[21] Appl. No.: 569,117

[22] PCT Filed: Jun. 17, 1994

[86] PCT No.: PCT/EP94/01978

§ 371 Date: Dec. 20, 1995

§ 102(e) Date: Dec. 20, 1995

[87] PCT Pub. No.: WO95/01353

PCT Pub. Date: Jan. 12, 1995

Related U.S. Application Data

[63] Continuation-in-part of Ser. No. 85,223, Jun. 30, 1993, abandoned.

[51] Int. Cl.$^6$ .................... C07D 471/04; C07D 487/04; A61K 31/47
[52] U.S. Cl. .................................................. 540/522
[58] Field of Search ................................. 540/522

[56] References Cited

FOREIGN PATENT DOCUMENTS

| | | | |
|---|---|---|---|
| 0051301 | 5/1982 | European Pat. Off. | C07C 103/52 |
| 0160307 | 11/1985 | European Pat. Off. | C07K 5/00 |
| 0187037 | 7/1986 | European Pat. Off. | C07K 5/06 |
| 481522 | 4/1992 | European Pat. Off. | C07D 471/04 |
| 534363 | 3/1993 | European Pat. Off. | C07K 5/06 |
| 0534396 | 3/1993 | European Pat. Off. | C07K 5/06 |
| 0534492 | 3/1993 | European Pat. Off. | C07K 5/06 |
| 0595610 | 5/1994 | European Pat. Off. | C07D 471/04 |
| 2448533 | 9/1980 | France | C07D 215/48 |

OTHER PUBLICATIONS

J. Med. Chem., vol. 27, pp. 816–818 (1984), Watthey et al.

*Primary Examiner*—Robert T. Bond
*Attorney, Agent, or Firm*—Norbert Gruenfeld

[57] ABSTRACT

Disclosed are the compounds of formula I wherein

X represents oxo, one hydroxy or lower alkoxy and one hydrogen, or two hydrogens;

$R_a$ and $R_b$ independently represent hydrogen, hydroxy, lower alkoxy, nitro, amino or halogen; or $R_a$ and $R_b$ on adjacent carbons taken together represent lower alkylenedioxy;

$R_c$ represents hydrogen, lower alkyl or aryl-lower alkyl;

R represents hydrogen or acyl;

$R_1$ represents hydrogen, lower alkyl, aryl, aryl-lower alkyl, cycloalkyl, cycloalkyl-lower alkyl, biaryl, biaryl-lower alkyl or trifluoromethyl;

$R_2$ represents hydrogen or lower alkyl; or $R_1$ and $R_2$ together with the carbon to which they are attached represent cycloalkylene or benzo-fused cycloalkylene;

m represents one or two;

n represents zero or one;

COOR$_3$ represents carboxyl or carboxyl derivatized in form of a pharmaceutically acceptable ester; disulfide derivatives formed from said compounds wherein R is hydrogen;

and pharmaceutically acceptable salts thereof;

pharmaceutical compositions comprising said compounds; methods for preparation of said compounds; intermediates; and methods of treating disorders in mammals which are responsive to ACE and NEP inhibition by administration of said compounds to mammals in need of such treatment.

12 Claims, No Drawings

ANTIHYPERTENSIVE TRICYCLIC AZEPINE DERIVATIVES USEFUL AS INHIBITORS OF ENKEPHALINASE AND ACE

CROSS-REFERENCE TO RELATED APPLICATIONS

This international application is a continuation-in-part of application number 08/085,223 filed Jun. 30, 1993, now abandoned.

SUMMARY OF THE INVENTION

The present invention is directed to novel tricyclic azepine derivatives described below which are useful as angiotensin converting enzyme (ACE) inhibitors and as neutral endopeptidase (NEP, EC 3.4.24.11) inhibitors. The compounds of the invention are particularly useful for the treatment of conditions which are responsive to ACE and NEP inhibition, particularly cardiovascular disorders, such as hypertension, renal insufficiency (including edema and salt reduction), pulmonary edema and congestive heart failure.

By virtue of their inhibition of neutral endopeptidase, the compounds of the invention may also be useful for the treatment of pain, depression, certain psychotic conditions, and cognitive disorders. Other potential indications include the treatment of angina, premenstrual syndrome, Meniere's disease, hyperaidosteronism, hypercalciuria, ascites, glaucoma, asthma and gastrointestinal disorders such as diarrhea, initable bowel syndrome and gastric hyperacidity.

DETAILED DESCRIPTION OF THE INVENTION

The present invention relates to the azepino[3,2,1-hi]indole and 1H-pyrido-[3,2,1-jk][1]benzazepine derivatives of the formula I (I)

[Structure showing tricyclic compound with substituents $R_a$, $R_b$, $R_c$, X, $(CH_2)_m$, N, $COOR_3$, =O, $NH-CO-C(R_1)(R_2)-(CH_2)_nS-R$]

wherein

X represents oxo, one hydroxy or lower alkoxy and one hydrogen, or two hydrogens;

$R_a$ and $R_b$ independently represent hydrogen, hydroxy, lower alkoxy, nitro, amino or halogen; or $R_a$ and $R_b$ on adjacent carbons taken together represent lower alkylenedioxy;

$R_c$ represents hydrogen, lower alkyl or aryl-lower alkyl;

R represents hydrogen or acyl;

$R_1$ represents hydrogen, lower alkyl, aryl, aryl-lower alkyl, cycloalkyl, cycloalkyl-lower alkyl, biaryl, biaryl-lower alkyl or trifluoromethyl;

$R_2$ represents hydrogen or lower alkyl; or $R_1$ and $R_2$ together with the carbon to which they are attached represent cycloalkylene or benzo-fused cycloalkylene;

m represents one or two;

n represents zero or one;

$COOR_3$ represents carboxyl or carboxyl derivatized in form of a pharmaceutically acceptable ester; disulfide derivatives formed from said compounds wherein R is hydrogen;

and pharmaceutically acceptable salts thereof.

The present invention is also directed to methods for preparation of said compounds; intermediates; methods of treating disorders in mammals which are responsive to ACE and NEP inhibition by administration of said compounds to mammals in need of such treatment; pharmaceutical compositions; and processes for the manufacture of pharmaceutical compositions.

Pharmaceutically acceptable esters are preferably prodrug ester derivatives, such being convertible by solvolysis or under physiological conditions to the free carboxylic acids of formula I.

Pharmaceutically acceptable prodrug esters are preferably e.g. lower alkyl esters, α-(lower alkanoyloxy)-lower alkyl esters, such as the methyl ester, pivaloyloxy-methyl ester, and α-(lower alkoxycarbonyl- or di-alkylamino carbonyl)-lower alkyl esters.

Pharmaceutically acceptable salts are salts derived from pharmaceutically acceptable bases for any acidic compounds of the invention, e.g. those wherein $COOR_3$ represents carboxyl. Such are e.g. alkali metal salts (e.g. sodium, potassium salts), alkaline earth metal salts (e.g. magnesium, calcium salts), amine salts (e.g. tromethamine salts).

The definitions used herein, unless denoted otherwise, have the following meanings within the scope of the present invention.

Aryl represents carbocyclic or heterocyclic aryl.

Carbocyclic aryl represents preferably monocyclic carbocyclic aryl or optionally substituted naphthyl.

Monocyclic carbocyclic aryl represents optionally substituted phenyl, being preferably phenyl or phenyl substituted by one to three substituents, such being advantageously lower alkyl, hydroxy, lower alkoxy, lower alkanoyloxy, halogen, cyano, trifluoromethyl, lower alkanoylamino, lower alkyl-(thio, sulfinyl or sulfonyl) or lower alkoxycarbonyl.

Optionally substituted naphthyl represents 1- or 2-naphthyl or 1- or 2-naphthyl preferably substituted by lower alkyl, lower alkoxy or halogen.

Heterocyclic aryl represents preferably monocyclic heterocyclic aryl such as optionally substituted thienyl, furanyl or pyridyl.

Optionally substituted furanyl represents 2- or 3-furanyl or 2- or 3-furanyl preferably substituted by lower alkyl.

Optionally substituted pyridyl represents 2-, 3- or 4-pyridyl or 2-, 3- or 4-pyridyl preferably substituted by lower alkyl, halogen or cyano.

Optionally substituted thienyl represents 2- or 3-thienyl or 2- or 3-thienyl preferably substituted by lower alkyl.

Aryl as in aryl-lower alkyl is preferably phenyl or phenyl substituted by one or two of lower alkyl, lower alkoxy, hydroxy, lower alkanoyloxy, halogen, trifluoromethyl, cyano, lower alkanoylamino or lower alkoxycarbonyl; also, optionally substituted naphthyl.

Aryl-lower alkyl is advantageously benzyl or 1- or 2-phenethyl optionally substituted on phenyl by one or two of lower alkyl, lower alkoxy, hydroxy, lower alkanoyloxy, halogen or trifluoromethyl.

The term "lower" referred to herein in connection with organic radicals or compounds respectively defines such with up to and including 7, preferably up and including 4 and advantageously one or two carbon atoms. Such may be straight chain or branched.

A lower alkyl group preferably contains 1–4 carbon atoms and represents for example ethyl, propyl, butyl or advantageously methyl.

Lower alkylenedioxy represents preferably methylenedioxy or ethylenedioxy.

A lower alkoxy group preferably contains 1–4 carbon atoms and represents for example methoxy, propoxy, isopropoxy or advantageously ethoxy.

Cycloalkyl represents a saturated cyclic hydrocarbon radical, for example, $C_3$–$C_7$cycloalkyl, which preferably contains 5 to 7 ring carbons and is, preferably cyclopentyl or cyclohexyl.

The term cycloalkyl-lower alkyl represents for example, $C_3$–$C_7$cycloalkyl-lower alkyl, preferably 1- or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)-butyl.

A lower alkoxycarbonyl group preferably contains 1 to 4 carbon atoms in the alkoxy portion and represents, for example, methoxycarbonyl, propoxycarbonyl, isopropoxycarbonyl or advantageously ethoxycarbonyl.

Halogen (halo) preferably represents fluoro or chloro, but may also be bromo or iodo.

Acyl is derived from a carboxylic acid and represents preferably lower alkanoyl, carbocyclic aryl-lower alkanoyl, aroyl, lower alkoxycarbonyl or aryl-lower alkoxycarbonyl, advantageously lower alkanoyl or aroyl. Acyl also represents lower alkanoyl (preferably acetyl) substituted, preferably at the α-position, by e.g. lower alkoxy, aryl-lower alkoxy, hydroxy, lower alkanoyloxy, di-lower alkylamino, lower alkanoylamino, morpholino, piperidino, pyrrolidino, 1-lower alkylpiperazino or lower alkylthio.

Lower alkanoyl is preferably acetyl, propionyl, butyryl, or pivaloyl.

Lower alkanoyl substituted by lower alkoxy is preferably (methoxy- or ethoxy-)acetyl.

Aroyl is carbocyclic or heterocyclic aroyl, preferably monocyclic carbocyclic or monocyclic heterocyclic aroyl.

Monocyclic carbocyclic aroyl is preferably benzoyl or benzoyl substituted by lower alkyl, lower alkoxy, halogen or trifluoromethyl.

Monocyclic heterocyclic aroyl is preferably pyridylcarbonyl or thienylcarbonyl.

Aryl-lower alkoxycarbonyl is preferably monocyclic carbocyclic-lower alkoxycarbonyl, advantageously benzyloxycarbonyl.

Biaryl represents monocarbocyclic aryl substituted by monocyclic carbocyclic or monocyclic heterocyclic aryl, and preferably represents biphenylyl, advantageous 4-biphenylyl optionally substituted on one or both benzene rings by lower alkyl, lower alkoxy, halogen or trifluoromethyl.

Biaryl-lower alkyl is preferably 4-biphenylyl-lower alkyl, advantageously 4-biphenylyl-methyl.

Cycloalkylene (as used for ring combined —C($R_1$, $R_2$)— of the side chain e.g. in formula I) represents $C_3$–$C_7$-cycloalkylene, preferably cyclopentylene or cyclohexylene.

Benzo-fused cycloalkylene (as used for ring combined —C($R_1$, $R_2$)— of the side chain e.g. in formula I) represents preferably benzo-fused cyclopentylene or benzo-fused cyclohexylene (1,1- or 2,2-indanylene or 1,1- or 2,2-tetralinylene).

Compounds of formula I, depending on the nature of substituents, possess two or more asymmetric carbon atoms. The resulting diastereomers and optical antipodes are encompassed by the instant invention.

Preferred are the compounds of formula I, derivatives and salts thereof wherein the substituents at the starred (*) positions have the S-configuration as represented by formula Ia $$\text{(Ia)}$$

wherein X, $R_a$, $R_b$, $R_c$, R, $R_1$, $R_2$, m, n and $COOR_3$ have the meanings as defined above.

Particular embodiments of the invention relate to azepino[3,2,1-hi]indole derivatives (wherein m represents one) and furthermore 1H-pyrido[3,2,1-jk][1]benzazepine derivatives (wherein m represents 2).

Further preferred are compounds of formula Ia, derivatives and salts thereof, wherein the optically active carbon atom attached to which are radicals $R_1$ and $R_2$ has the (S)-configuration, provided that the meanings of $R_1$ and $R_2$ are different.

Further particular embodiments of the invention relate to compounds wherein n represents zero; also wherein n represents 1.

Preferred are the said compounds wherein

X represents oxo, one hydroxy or lower alkoxy and one hydrogen, or two hydrogens;

$R_a$ and $R_b$ independently represent hydrogen, hydroxy, lower alkoxy, nitro, amino or halogen; or $R_a$ and $R_b$ on adjacent carbons taken together represent lower alkylenedioxy;

$R_c$ represents hydrogen, lower alkyl, phenyl-lower alkyl in which phenyl is unsubstituted or substituted by one or two substituent(s) selected from the group consisting of lower alkyl, lower alkoxy, hydroxy, lower alkanoyloxy, halogen, trifluoromethyl, cyano, lower alkanoylamino and lower alkoxycarbonyl, or naphthyl-lower alkyl in which naphthyl is unsubstituted or substituted by lower alkyl, lower alkoxy or halogen;

R represents hydrogen, lower alkanoyl, lower alkanoyl which is substituted by a substituent selected from the group consisting of lower alkoxy, phenyl-lower alkoxy, hydroxy, lower alkanoyloxy, di-lower alkylamino, lower alkanoylamino, morpholino, piperidino, pyrrolidino, 1-lower alkylpiperazino and lower alkylthio, phenyl-lower alkanoyl in which phenyl is unsubstituted or substituted by one or two substituent (s) selected from the group consisting of lower alkyl, lower alkoxy, hydroxy, lower alkanoyloxy, halogen, trifluoromethyl, cyano, lower alkanoylamino and lower alkoxycarbonyl, benzoyl, benzoyl substituted by a substituent selected from the group consisting of lower alkyl, lower alkoxy, halogen and trifluoromethyl, pyridylcarbonyl, or thienylcarbonyl, lower alkoxycarbonyl, or phenyl-lower alkoxycarbonyl in which phenyl is unsubstituted or substituted by one or two substituent(s) selected from the group consisting of lower alkyl, lower alkoxy, hydroxy, lower alkanoyloxy, halogen, trifluoromethyl, cyano, lower alkanoylamino and lower alkoxycarbonyl;

$R_1$ represents hydrogen, lower alkyl, phenyl, phenyl substituted by one to three substituents selected from the group consisiting of lower alkyl, hydroxy, lower alkoxy, lower alkanoyloxy, halogen, cyano, trifluoromethyl, lower alkanoylamino, lower alkyl-(thio, sulfinyl or sulfonyl) and lower alkoxycarbonyl, naphthyl, naphthyl substituted by lower alkyl, lower alkoxy or halogen, thienyl, pyridyl, phenyl-lower alkyl in which phenyl is unsubstituted or substituted by one or two substituents selected from the group consisiting of lower alkyl, hydroxy, lower alkoxy, lower alkanoyloxy, halogen, cyano, trifluoromethyl, lower alkanoylamino, and lower alkoxycarbonyl, $C_3$–$C_7$cycloalkyl, $C_3$–$C_7$cycloalkyl-lower alkyl, biphenylyl which unsubstituted or substituted on one or both benzene rings by lower alkyl, lower alkoxy, halogen or trifluoromethyl, biphenylyl-lower alkyl in which biphenylyl which unsubstituted or substituted on one or both benzene rings by lower alkyl, lower alkoxy, halogen or trifluoromethyl, or is trifluoromethyl;

$R_2$ represents hydrogen or lower alkyl; or $R_1$ and $R_2$ together with the carbon to which they are attached represent $C_3$–$C_7$cycloalkylene, or benzofused $C_3$–$C_7$cycloalkylene;

m represents one or two;

n represents zero or one;

$COOR_3$ represents carboxyl, lower alkyl ester of carboxyl, α-(lower alkanoyloxy-)-lower alkyl ester of carboxyl or α-(lower alkoxycarbonyl- or di-lower alkylamino-carbonyl)-lower alkyl ester of carboxyl; disulfide derivatives formed from said compounds wherein R is hydrogen;

and pharmaceutically acceptable salts thereof.

Preferred are the said compounds wherein

X represents oxo, one hydroxy or lower alkoxy and one hydrogen, or two hydrogens;

$R_a$, $R_b$ and $R_c$ independently represent hydrogen;

R represents hydrogen, lower alkanoyl, lower alkoxy-lower alkanoyl, benzoyl, thienylcarbonyl, pyridylcarbonyl, or morpholino-lower alkanoyl;

$R_1$ represents lower alkyl, phenyl-lower alkyl, $C_3$–$C_7$cycloalkyl, $C_3$–$C_7$cycloalkyl-lower alkyl, 4-biphenylylmethyl, or trifluoromethyl;

$R_2$ represents hydrogen; or $R_1$ and $R_2$ together with the carbon atom to which they are attached represent $C_5$- or $C_6$-cycloalkylene;

m represents one or two;

n represents zero or one;

$R_3$ represents hydrogen or lower alkyl;

and pharmaceutically acceptable salts thereof.

Preferred are the said compounds wherein $R_a$, $R_b$ and $R_c$ represent hydrogen; X represents two hydrogens; R represents hydrogen, lower alkanoyl, lower alkoxy-lower alkanoyl, or heterocyclic or carbocyclic aroyl; $R_1$ represents carbocyclic aryl-lower alkyl, cyclohexyl-lower alkyl, biphenylyl-lower alkyl or lower alkyl; $R_2$ represents hydrogen; n represents zero or one; $COOR_3$ represents carboxyl, lower alkoxycarbonyl, α-(lower alkanoyloxy)- or α-(lower alkoxycarbonyl or di-lower alkylamino carbonyl)-lower alkoxycarbonyl; and pharmaceutically acceptable salts thereof.

Particularly preferred are the compounds of formula Ia wherein $R_a$, $R_b$ and $R_c$ represent hydrogen; X represents two hydrogens; R represents hydrogen, acetyl, methoxyacetyl or benzoyl; $R_1$ represents cyclohexyl-methyl, benzyl or benzyl substituted by hydroxy, halogen, lower alkyl, lower alkoxy, lower alkanoyloxy or trifluoromethyl; $R_2$ represents hydrogen; m represents one or two; n represents zero; and $COOR_3$ represents carboxyl or pivaloyloxymethoxycarbonyl; and pharmaceutically acceptable salts thereof.

Particularly preferred are the compounds of formula Ia wherein $R_a$, $R_b$ and $R_c$ each represent hydrogen; X represents two hydrogens; R represents hydrogen or acetyl; $R_1$ represents cyclohexyl-methyl, benzyl or benzyl substituted by hydroxy, halogen, lower alkyl, lower alkoxy, lower alkanoyloxy or trifluoromethyl; $R_2$ represents hydrogen; m represents one; n represents zero; and $R_3$ represents hydrogen; and pharmaceutically acceptable salts thereof.

The novel compounds of the invention are angiotensin converting enzyme (ACE) inhibitors inhibiting the conversion of angiotensin I to the pressor substance angiotensin II and thus decrease blood pressure in mammals. Furthermore, compounds of the invention demonstrate inhibition of neutral endopeptidase (NEP) and thus potentiate the cardiovascular (e.g. diuretic and natriuretic) effects of atrial natriuretic factors (ANF). The combined effect is beneficial for the treatment of cardiovascular disorders in mammals, in particular hypertension and cardiac conditions such as congestive heart failure.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously orally or intravenously, e.g. as a suspension or in aqueous solution. The dosage in vitro may range between about $10^{-5}$ molar and $10^{-9}$ molar concentrations. The dosage in vivo may range depending on the route of administration, between about 0.01 and 50 mg/kg, advantageously between about 0.1 and 30 mg/kg.

In vitro testing is most appropriate for the free carboxylic acids of the invention. The test compound is dissolved in dimethyl sulfoxide, ethanol, or 0.25M sodium bicarbonate solution, and the solution is diluted with buffer to the desired concentration.

The in vitro inhibition of the angiotensin-converting enzyme by the compounds of this invention can be demonstrated by a method analogous to that given in Biochem. Pharmacol. 20: 1637, 1971. The buffer for the ACE assay is 300 mM NaCl, 100 NM $KH_2PO_4$ (pH 8.3). The reaction is initiated by the addition of 100 µl of hippuryl-histidyl-leucine (2 mg/ml) to tubes containing enzyme and drug in a volume of 150 µl and tubes are incubated for 30 minutes at 37° C. The reaction is terminated by the addition of 0.75 ml 0.6N NaOH. 100 µl of freshly prepared O-pthaldehyde solution (2 mg/ml in methanol) is added to the tubes, the contents are mixed and allowed to stand at room temperature. After 10 minutes, 100 µl of 6N HCl is added. The tubes are centrifuged and the supernatant optical density is read at 360 nm. The results are plotted against drug concentration to determine the $IC_{50}$, i.e., the drug concentration which gives half the activity of the control sample containing no drug. Illustrative of the invention, the compounds of examples 2(a) and 5(a) demonstrate an $IC_{50}$ of about 30 nM and the compound of example 6(b) demonstrates an $IC_{50}$ of about 77 nM in the inhibiting ACE in vitro assay.

Inhibition of angiotensin convening enzyme can be demonstrated in vivo on oral or intravenous administration by measuring inhibition of the angiotensin I induced pressor response in normotensive rats.

The in vivo test for intravenously administered compounds is performed with male, normotensive rats, which are anesthetized with sodium metofan. A femoral artery and femoral vein are cannulated respectively for direct blood pressure measurement on i.v. administration of Angiotensin I and i.v. or p.o. administration of a compound of this invention. After the basal blood pressure is stabilized, pressor responses to 3 challenges of 300 ng/kg angiotensin I i.v., at 15 minute intervals, are obtained. Such pressure responses are usually again obtained at 15, 30, 60 and 90 minutes, and then every hour up to 6 hours after i.v. or p.o. administration of the compound to be tested, and compared with the initial responses. Any observed decrease of said pressor response is an indication of Angiotensin I converting enzyme inhibition.

The in vitro inhibition of neutral endopeptidase (NEP, EC 3.4.24.11) can be determined as follows:

Neutral endopeptidase 3.4.24.11 activity is determined by the hydrolysis of the substrate glutaryl-Ala-Ala-Phe-2-naphthylamide (GAAP) using a modified procedure of Orlowski and Wilk (1981). The incubation mixture (total volume 125 µl) contains 4.2 µg of protein (rat kidney cortex membranes prepared by method of Maeda et at, 1983), 50 mM tris buffer, pH 7.4 at 25° C., 500 µM substrate (final concentration), and leucine aminopeptidase M (2.5 µg). The mixture is incubated for 10 minutes at 25° C. and 100 µl of fast garnet (250 µg fast garnet/ml of 10% Tween 20 in 1M sodium acetate, pH 4.2) is added. Enzyme activity is measured spectrophotometrically at 540 nm. One unit of NEP 24.11 activity is defined as 1 nmol of 2-naphthylamine released per minute at 25° C. at pH 7.4. $IC_{50}$ values are determined, i.e. the concentration of test compound required for 50% inhibition of the release of 2-naphthylamine.

Neutral endopeptidase activity can also be determined using ANF as a substrate. Atrial natriuretic factor degrading activity is determined by measuring the disappearance of rat-ANF (r-ANF) using a 3 minute reverse phase-HPLC separation. An aliquot of the enzyme in 50 mM Tris HCl buffer, pH 7.4, is preincubated at 37° C. for 2 minutes and the reaction is initiated by the addition of 4 nmol of r-ANF in a total volume of 50 µl. The reaction is terminated after 4 minutes with the addition of 30 µl of 0.27% trifluoroacetic acid (TFA). One unit of activity is defined as the hydrolysis of 1 nmol of r-ANF per minute at 37° C. at pH 7.4. $IC_{50}$ values are determined, i.e. the concentration of test compound required for 50% inhibition of the hydrolysis of ANF.

Illustrative of the invention, the compound of example 2(a) demonstrates an $IC_{50}$ of about 50 nM and the compound of example 6(b) demonstrates an $IC_{50}$ of about 15 nM in the GAAP in vitro assay.

The effect of the compounds of the invention on rat plasma ANF concentration can be determined as follows:

Male Sprague-Dawley rats (275–390 g) are anesthetized with ketamine (150 mg/kg)/acepromazine (10%) and instrumented with catheters in the femoral artery and vein to obtain blood samples and infuse ANF, respectively. The rats are tethered with a swivel system and are allowed to recover for 24 hours before being studied in the conscious, unrestrained state.

In the assay, plasma ANF levels are determined in the presence and absence of NEP inhibition. On the day of study, all rats are infused continuously with ANF at 450 ng/kg/min. i.v. for the entire 5 hours of the experiment. Sixty minutes after beginning the infusion, blood samples for baseline ANF measurements are obtained (time 0) and the rats are then randomly divided into groups treated with the test compound or vehicle. Additional blood samples are taken 30, 60, 120, 180, and 240 minutes after administration of the test compound.

Plasma concentrations are determined by a specific radioimmunoassay. The plasma is diluted (X 12.5, X 25 and X 50) in buffer containing: 50 mM Tris (pH 6.8), 154 mM NaCl, 0.3% bovine serum albumin, 0.01% EDTA. One hundred microliters of standards [rANF (99–126)] or samples are added to 100 µl of rabbit anti-rANF serum and incubated at 4° C. for 16 hours. Ten thousand cpm of [$^{125}$I]rANF are then added to the reaction mixture which is incubated at 4° C. for an additional 24 hours. Goat anti-rabbit IgG serum coupled to paramagnetic particles is added to the reaction mixture and bound [$^{125}$I]rANF is pelleted by exposing the mixture to an attracting magnetic rack. The supernatant is decanted and the pellets counted in a gamma counter. All determinations are performed in duplicate. Plasma ANF levels are expressed as a percent of those measured in vehicle-treated animals which received ANF alone (450 ng/kg/min i.v.).

The antihypertensive activity can be determined e.g. in the spontaneously hypertensive rat and the DOCA-salt hypertensive rat, e.g. according to Trapani et at, J. Cardiovasc. Pharmacol. 14, 419–424 (1989).

The diuretic (saluretic) activity can be determined in standard diuretic screens, e.g. as described in "New Antihypertensive Drugs", Spectrum Publications, 1976, pages 307–321, or by measuring the potentiation of atrial natriuretic factor-induced natriuresis and diuresis in the rat.

The antihypertensive effect can be determined in desoxycorticosterone acetate (DOCA)-salt hypertensive rats as follows:

DOCA-salt hypertensive rats (280–380 g) are prepared by the standard method. Rats underwent a unilateral nephrectomy and one week later are implanted with silastic pellets containing 100 mg/kg of DOCA. The rats are maintained on 1% NaCl/0.2% KCl drinking water for three to five weeks until sustained hypertension is established. The antihypertensive activity is evaluated at this time.

Two days before an experiment, the rats are anesthetized with methoxyflurane and instrumented with catheters in the fern oral artery to measure arterial blood pressure. Forty-eight hours later, baseline arterial pressure and heart rate are recorded during a 1 hour period. The test compound or vehicle is then administered and the same cardiovascular parameters are monitored for an additional 5 hours.

The antihypertensive effect can also be determined in spontaneously hypertensive rats by indirect measurement of systolic pressure. Conscious rats are placed individually in restraint cages within a gently warmed chamber. A rubber pulse sensor is placed distal to an inflatable occlusive cuff on each rat's tail. The cuff is periodically inflated to occlude the tail artery, and systolic pressure is recorded as the point where the first discernible pulse emerges along the decaying calibrated pressure curve. After obtaining control values of blood pressure and heart rate, test compounds are administered orally once daily for 4 consecutive days. Additional blood pressure measurements are usually made at 2.0, 4.0 and 23.5 hours after each daily dosing, and responses are compared to those of rats dosed with the treatment vehicle.

The potentiation of the natriuretic effect of ANF can be determined as follows:

Male Sprague-Dawley rats (280–360 g) are anesthetized with Inactin (100 mg/kg i.p.) and instrumented with catheters in the femoral artery, femoral vein and urinary bladder to measure arterial pressure, administer ANF and collect urine, respectively. A continuous infusion of normal saline (33 µl/min) is maintained throughout the experiment to promote diuresis and sodium excretion. The experimental protocol consists of an initial 15 minute collection period (designated as pre-control) followed by three additional collection periods. Immediately after completion of the pre-control period, test compound or vehicle is administered; nothing is done for the next 45 minutes. Then, blood pressure and renal measurements are obtained during a second collection period (designated control; 15 minutes). At the conclusion of this period, ANF is administered (1 μg/kg i.v. bolus) to all animals and medal pressure and renal parameters are determined during two consecutive 15 minutes collection periods. Mean arterial pressure, urine flow and urinary sodium excretion are determined for all collection periods. Blood pressure is measured with a Gould p50 pressure transducer, urine flow is determined gravimetrically, sodium concentration is measured by flame photometry, and urinary sodium excretion is calculated as the product of urine flow and urine sodium concentration.

The compounds of the invention can be prepared by condensing a compound of formula II

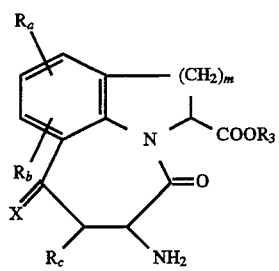

wherein $R_a$, $R_b$, $R_c$, m and X have meaning as defined above and $COOR_3$ represents esterified carboxyl, with a carboxyl acid of the formula III

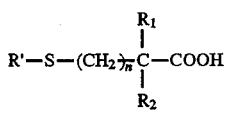

wherein $R_1$, $R_2$ and n have meaning as defined above, and R' represents acyl or optionally substituted benzyl or a reactive functional derivative of said carboxylic acid; and converting a resulting product wherein R' is optionally substituted benzyl to a compound of formula I wherein R is hydrogen; and in above said process, if temporarily protecting any interfering reactive group(s), removing said protecting group(s), and then isolating the resulting compound of the invention; and, if desired, converting any resulting compound of the invention into another compound of the invention; and/or, if desired, converting a free carboxylic acid function into a pharmaceutically acceptable ester derivative, or converting a resulting ester into the free acid or into another ester derivative; and/or, if desired, converting a resulting free compound into a salt or a resulting salt into the free compound or into another salt, and/or, if desired, separating a mixture of isomers or racemates obtained into the single isomers or racemates, and/or, if desired, resolving a racemate obtained into the optical antipodes.

In starting compounds and intermediates which are converted to the compounds of the invention in manner described herein, functional group present, such as thiol, carboxyl, amino and hydroxy groups, are optionally protected by conventional protecting groups that are common in preparative organic chemistry. Protected thiol, carboxyl, amino and hydroxy groups are those that can be converted under mild conditions into free thiol, carboxyl, amino and hydroxy groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (thiol, carboxyl, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, N.Y. 1973, T. W. Greene and P. G. M. Woots, "Protective Groups in Organic Synthesis", Wiley, N.Y. 1991, and also in "The Peptides", Vol. I, Schroeder and Luebke, Academic Press, London, N.Y., 1965.

The preparation of compounds of the invention involving the condensation of an amine of formula II with the acid of formula III, or a functional reactive derivative thereof, is carried out by methodology well-known for peptide synthesis.

Reactive derivatives of carboxylic acids of the formula III are, for example, activated esters or reactive anhydrides derived therefrom, and also reactive cyclic amides.

Activated esters of compounds of the formula III are in particular esters which are unsaturated at the linking carbon atom of the esterifying radical, for example of the vinyl ester type, such as vinyl esters (obtainable, for example, by transesterification of an appropriate ester with vinyl acetate; activated vinyl ester method), carbamoylvinyl esters (obtainable, for example, by treating the appropriate acid with an isoxazolium reagent; 1,2-oxazolium or Woodward method) or 1-lower alkoxyvinyl esters (obtainable, for example, by treating the appropriate acid with a lower alkoxyacetylene; ethoxyacetylene method), or esters of the amidino type, such as N,N'-disubstituted amidino esters (obtainable, for example, by treating the appropriate acid with a suitable N,N'-disubstituted carbodiimide, for example N,N'-dicyclohexylcarbodiimide; carbodiimide method) or N,N-disubstituted amidino esters (obtainable, for example, by treating the appropriate acid with an N,N-disubstituted cyanamide; cyanamide method), suitable aryl esters, in particular phenyl esters substituted by electron-attracting substituents (obtainable, for example, by treating the appropriate acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensing agent, such as N,N'-dicyclohexylcarbodiimide; activated aryl ester method), cyanomethyl esters (obtainable, for example, by treating the appropriate acid with chloroacetonitrile in the presence of a base; cyanomethyl ester method), thio esters, in particular phenylthio esters which are unsubstituted or substituted, for example by nitro, (obtainable, for example, by treating the appropriate acid with thiophenols which are unsubstituted or substituted, for example by nitro, inter alia with the aid of the anhydride or carbodiimide method; activated thiol ester method) or in particular amino or amido esters (obtainable, for example, by treating the appropriate acid with an N-hydroxyamino or N-hydroxyamido compound and their activated derivatives, for example N-hydroxysuccinimide, N-hydroxypiperidine, N-hydroxyphthalimide, N-hydroxy-5-norbornene- or norbonane-2,3-dicarboximide, 1-hydroxybenzotriazole or benzotriazol-1-yloxyphosphonium salts or benzotriazol-1-yluronium salts, or 3-hydroxy-3,4-dihydro-1,2,3-benzotriazin-4-one, for example by the anhydride or carbodiimide method; activated N-hydroxy ester method).

Anhydrides of acids can be symmetrical or preferably mixed anhydrides of these acids, for example anhydrides with inorganic acids, such as acid halides, in particular acid chlorides, (obtainable, for example, by treating the appropriate acid with thionyl chloride, phosphorus pentachloride or oxalyl chloride; acid chloride method), azides (obtainable, for example, from an appropriate acid ester via the corresponding hydrazide and its treatment with nitrous acid; azide method), anhydrides with carbonic acid half-esters, for example lower alkyl carbonate half-esters (obtainable, for example, by treating the appropriate acid with lower alkyl chloroformates or with a 1-lower alkoxycarbonyl-2-lower alkoxy-1,2-dihydroquinoline, for example 1-ethoxycarbonyl-2-ethoxy-1,2-dihydroquinoline; mixed O-alkylcarbonic anhydride method), anhydrides with dihalogenated, in particular dichlorinated, phosphoric acid (obtainable, for example, by treating the appropriate acid with phosphorus oxychloride; phosphorus oxychloride method), anhydrides with other phosphoric acid derivatives (for example those which can be obtained with phenyl N-phenylphosphoramidochloridate) or with phosphorus acid derivatives, or anhydrides with organic acids, such as mixed anhydrides with organic carboxylic acids (obtainable, for example, by treating the appropriate acid with a substituted or unsubstituted lower alkane- or phenyl-lower alkane carbonyl halide, for example phenylacetyl, pivaloyl or trifluoroacetyl chloride; mixed carbonic anhyride method) or with organic sulfonic acids (obtainable, for example, by treating a salt, such as an alkali metal salt, of the appropriate acid with a suitable organic sulfonyl halide, such as lower alkane- or arylsufonyl chloride, for example methane- or p-toluenesulfonyl chloride; mixed sulfonic anhydride method), and also symmetrical anhydrides (obtainable, for example, by condensation of the appropriate acid in the presence of a carbodiimide or of 1-diethylaminopropyne; symmetrical anhydride method).

Suitable cyclic amides are in particular amides having five-membered diazacyclic compounds of aromatic character, such as amides with imidazoles, for example imidazole (obtainable, for example, by treating the appropriate acid with N,N'-carbonyldiimidazole; imidazole method), or pyrazoles, for example 3,5-dimethylpyrazole (obtainable, for example, via the acid hydrazide by treating with acetylacetone; pyrazolide method).

The condensation reaction can be carried out in the presence of one of the customary condensing agents. Customary condensing agents are, for example, carbodiimides, for example diethyl-, dipropyl- or N-ethyl-N'-(3-dimethylaminopropyl)carbodiimide or in particular dicyclohexylcarbodiimide, and also suitable carbonyl compounds, for example carbonyldiimidazole, 1,2-oxazolium compounds, for example 2-ethyl-5-phenyl-1,2-oxazolium-3'-sulfonate and 2-tert-butyl-5-methylisoxazolium perchlorate, or a suitable acylamino compound, for example 2-ethoxy-1-ethoxycarbonyl-1,2-dihydroquinoline, and also activated phosphoric acid derivatives, for example diphenylphosphoryl azide, diethylphosphoryl cyanide, phenyl N-phenylphosphoramidochloridates, bis(2-oxo-3-oxazolidinyl)phosphinoyl chloride or 1-benzotriazolyloxy-tris(dimethylamino)phosphonium hexafluorophosphate.

If desired, an organic base is added, for example a tri-lower alkylamine, for example triethylamine or ethyldiisopropylamine, or a heterocylic base, for example pyridine, 4-dimethylaminopyridine or preferably N-methylmorpholine.

The condensation of acid anhydrides with amines can be carried out, for example, in the presence of inorganic carbonates, for example alkali metal carbonates or hydrogen-carbonates, such as sodium or potassium carbonate or hydrogencarbonate (customarily together with a sulfate).

The condensation reaction is preferably carried out in an inert polar aprotic, preferably anhydrous, solvent or solvent mixture, for example in a carboxamide, for example formamide or dimethylformamide, a halogenated hydrocarbon, for example methylene chloride, carbon tetrachloride or chlorobenzene, a ketone, for example acetone, cyclic ethers, for example tetrahydrofuran, an ester, for example ethyl acetate, or a nitrile, for example acetonitrile, or in mixtures thereof, if desired at reduced or elevated temperature, for example in a temperature range from about −40° C. to about +100° C., preferably from about −10° C. to about +50° C., and if desired under an inert gas atmosphere, for example a nitrogen atmosphere.

Reactive acid derivatives can also be formed in situ.

The condensation of an amino ester of formula II with a free carboxylic acid of formula III is carried out advantageously in the presence of a condensing agent such as dicyclohexylcarbodiimide or N-(3-dimethylaminopropyl)-N'-ethylcarbodiimide and hydroxybenzotriazole, or benzotriazol-1-yloxytris(dimethylamino)phosphonium hexafluorophosphate (BOP Reagent) and triethylamine, in an inert polar solvent such as dimethylformamide of methylene chloride, preferably at room temperature.

The condensation of an amino ester of formula II with a reactive functional derivative of an acid of formula III in the form of an acid halide, advantageously an acid chloride, or mixed anhydride, is carried out in an inert solvent such as toluene or methylene chloride, advantageously in the presence of a base, e.g. an inorganic base such as potassium carbonate or an organic base such as triethylamine or pyridine, preferably at room temperature.

Reactive functional derivatives of carboxylic acids of formula III are preferably acid halides (e.g. the acid chloride) and mixed anhydrides, such as the pivaloyl or isobutyl-oxycarbonyl anhydride, or activated esters such as benzotriazole or hexafluorophenyl ester.

The starting material of formula II can be prepared according to methods described herein and illustrated in the examples.

The preparation involves the acylation of an ester of an indoline-2-carboxylic acid or a tetrahydroquinoline-2-carboxylic acid (preferably the optically active (S)-isomer) of formula IV

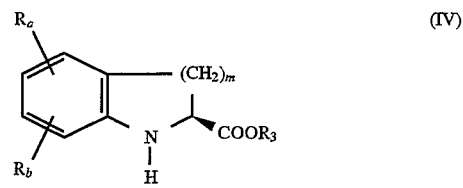

(IV)

wherein m, $R_a$ and $R_b$ have meaning as defined hereinabove and $COOR_3$ represents esterified carboxyl (e.g. wherein $R_3$ is lower alkyl) with an appropriately N- and β-carboxy-protected aspartic acid (preferably L-aspartic acid) of formula V

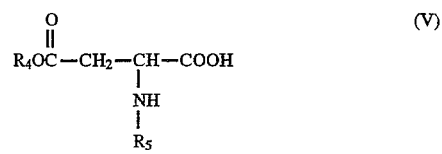

(V)

wherein $R_4$ is a labile carboxy protecting group, e.g. benzyl and $R_5$ is a labile amino protecting group, e.g. t-butoxycarbonyl to obtain a compound of formula VI

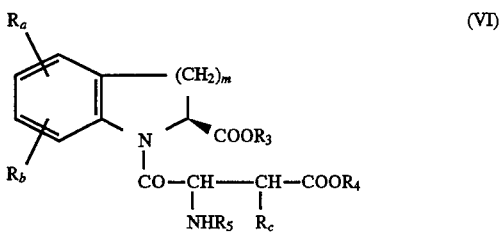

(VI)

wherein m, $R_a$, $R_b$ and $R_c$ have meaning as defined above, $COOR_3$ and $COOR_4$ represent esterified carboxy and $R_5$ represents an N-protecting group.

The N-protecting group is removed e.g. with anhydrous acid, such as trifluoroacetic acid, and the resulting amino diester is again N-protected by condensation with e.g. trifluoroacetic anhydride to obtain the N-trifluoroacetyl diester derivative.

The diester (e.g. wherein $R_4$ is benzyl and $R_3$ is lower alkyl) is then selectively converted by hydrogenolysis to the monocarboxylic acid of formula VII

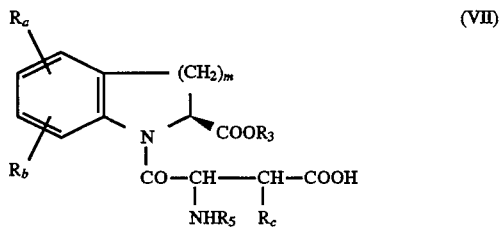

(VII)

wherein m, $R_a$, $R_b$, $R_c$, $R_3$ and $R_5$ have meaning as defined above, which is in turn converted to a reactive functional derivative (e.g. the acid chloride), and then cyclized under Friedel-Crafts acylation conditions, e.g. with aluminum trichloride, to yield an N-trifluoroacetyl protected derivative of formula II wherein X represents oxo.

The protected intermediate wherein X represents oxo may be converted to the corresponding intermediate wherein X represents one hydrogen and one hydroxy by reduction, e.g. with a metal hydride reducing agent such as sodium borohydride or by catalytic hydrogenation under mild conditions. The intermediate wherein X represents oxo can also be converted to the intermediate wherein X represents two hydrogens by catalytic hydrogenation in the presence of a palladium catalyst.

Said N-protected ester intermediate can be converted to a starting material of formula II, by treatment with an inorganic base such as lithium hydroxide to obtain the corresponding amino acid which is then reesterified with a lower alkanol, e.g. methanol in the presence of an anhydrous acid such as hydrogen chloride gas.

The starting tetrahydroquinoline-2-carboxylic acids and indoline-2-carboxylic acids (of formula IV wherein $R_3$ is hydrogen) in racemic or optically active form are known in the art or can be prepared according to methods known in the art, for instance as described in J. Med. Chem. 26, 1267 (1983).

The starting materials of formula III are known or if new may be prepared according to conventional methods. The starting materials wherein n=0 are prepared e.g. from the corresponding racemic or optically active α-amino acids, by conversion thereof to the α-bromo derivative followed by displacement thereof with the appropriate thio acids or optionally substituted benzylthiol, under basic conditions, for example as illustrated in European Patent application No. 524,553 published Jan. 27, 1993. The starting materials wherein n=1 can generally be prepared by addition of the thio-acid or optionally substituted benzylthiol to an optionally m-substituted acrylic acid ester. S-Debenzylation of the resulting final products is carried out by reductive cleavage, e.g. with Raney nickel in ethanol.

Certain compounds of the invention and intermediates can be converted to each other according to general reactions well known in the art.

The free mercaptans may be converted to the S-acyl derivatives by reaction of a reactive derivative of a carboxylic acid (corresponding to R being acyl in formula I), such as an acid anhydride or said chloride, preferably in the presence of cobalt chloride ($CoCl_2$) in an inert solvent such as acetonitrile or methylene chloride.

The free mercaptans, wherein R represents hydrogen, may be oxidized to the corresponding disulfides, e.g. by air oxidation or with the use of mild oxidation agents such as iodine in alcoholic solution. Conversely, disulfides may be reduced to the corresponding mercaptans, e.g. with reducing agents such as sodium borohydride, zinc and acetic acid or tributylphosphine.

Carboxylic acid esters may be prepared from a carboxylic acid by condensation with e.g. the halide corresponding to $R_3$, in the presence of a base, or with an excess of the corresponding alcohol, in the presence of an acid catalyst, according to methods well-known in the art.

Carboxylic acid esters and S-acyl derivatives may be hydrolyzed, e.g. with aqueous alkali such as alkali metal carbonates or hydroxides.

Compounds wherein X represents oxo can be converted to compounds wherein X is hydrogen and hydroxy or X is two hydrogens according to methodology described herein for intermediates.

In case mixtures of stereoisomers (e.g. diastereomers) are obtained, these can be separated by known procedures such as fractional crystallization and chromatography (e.g. thin layer, column, flash chromatography). Racemic free acids can be resolved into the optical antipodes by fractional crystallization of d- or 1-(α-methylbenzylamine, cinchonidine, cinchonine, quinine, quinidine, dehydroabietylamine, brucine or strychnine) salts and the like. Racemic products can also be resolved by chiral chromatography, e.g. high pressure liquid chromatography using a chiral adsorbent.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or superatmospheric pressure.

The invention relates in particular to the processes described in the examples.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being preferred. For example, the invention likewise relates to novel starting materials of formula II which have been specifically developed for the preparation of the compounds according to the invention, to their use and to processes for their preparation, the variables $R_a$, $R_b$, $R_c$, X, m, and $COOR_3$ having the meanings indicated for the preferred compound groups of the formulae I and Ia in each case.

The present invention additionally relates to the use in mammals of the compounds of the invention and their pharmaceutically acceptable, non-toxic acid addition salts, or pharmaceutical compositions thereof, as medicaments, such being angiotensin converting enzyme and neutral endopeptidase inhibitors e.g. for the treatment of cardiovascular disorders such as hypertension, edema, salt retention and congestive heart failure.

The present invention also relates to the use of the compounds of the invention for the preparation of pharmaceutical compositions especially pharmaceutical compositions having angiotensin converting enzyme and neutral endopeptidase inhibiting activity, and e.g. antihypertensive activity.

The pharmaceutical compositions according to the invention are those suitable for enteral, such as oral or rectal, transdermal and parenteral administration to mammals, including man, for the treatment of cardiovascular disorders, such as hypertension, comprising an effective amount of a pharmacologically active compound of the invention or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

A unit dosage for a mammal of about 50 to 70 kg may contain between about 5 and 50 mg of the active ingredient. The dosage of active compound is dependent on the species of warm-blooded animal (mammal), the body weight, age and individual condition, and on the form of administration.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. Optical rotations are measured at room temperature at 589 nm (D line of sodium) or other wavelengths as specified in the examples.

The prefixes R and S are used to indicate the absolute configuration at each asymmetric center.

EXAMPLE 1

(a) To a stirred solution of methyl 5-(S)-amino-1,2,4,5,6, 7-hexahydroazepino[3,2,1-hi]indol-4-one-2-(S)-carboxylate (1.45 g, 5.6 mmol) in DMF (30 mL) under nitrogen at 0° C., is added a solution of (S)-α-benzyl-S-acetylthioacetic acid (1.51 g, 6.7 mmol) in DMF (10 mL), followed by benzotriazol-1-yloxy-tris(dimethylamino)phosphonium hexafluorophosphate (BOP reagent, 2.97 g, 6.7 mmol) and triethylamine (1.9 mL, 13.4 mmol). The solution is allowed to warm up to room temperature over a 2 hour period, then stirred for 18 hours at room temperature. The solution is diluted with ethyl acetate (100 mL) and washed with ice-cold 0.5N HCl (50 mL). The aqueous layer is extracted with ethyl acetate (50 mL). The combined organic phases are successively washed with cold water (25 mL), a cold saturated solution of sodium bicarbonate (25 mL) and brine (20 mL). The organic phase is dried over anhydrous magnesium sulfate, filtered and concentrated under reduced pressure. The yellow solid residue is purified by flash-chromatography on silica gel eluting with ethyl acetate-hexane (3:7). The product is crystallized from ethyl acetate (15 mL) and hexane (30 mL) and dried under high vacuum at 50° C. for 1 hour to yield methyl 5-[((S)-2-acetylthio-3-phenylpropionyl)-(S)-amino]-1,2,4,5,6,7-hexahydroazepino-[3,2,1-hi]indol-4-one-2-(S)-carboxylate, m.p. 136°–138° C.; [α]$_D$=−174.23° (CHCl$_3$, c 0.09), having the following structure:

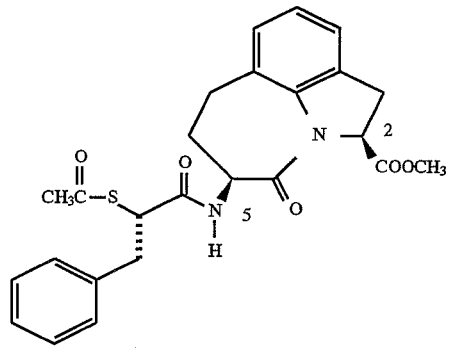

The starting material is prepared, for example, as follows:

To a stirred solution of (S)-N-t-BOC-aspartic acid β-benzyl ester (35 g, 108 mmol) in an ice-cold mixture of ethyl acetate (525 mL) and methylene chloride (70 mL) is added N-methylmorpholine (12 mL, 108 mmol), followed by isobutyl chloroformate (14 mL, 108 mmol). After 5 minutes, a mixture of (S)-indoline-2-carboxylic acid methyl ester hydrochloride salt (25 g, 113.4 mmol) and triethylamine (17.4 mL, 125 mmol) in methylene chloride (280 mL) is added rapidly. The resulting suspension is stirred for 90 minutes in an ice bath, then for 5 hours at room temperature. The reaction mixture is diluted with ethyl acetate (1.2 L) and poured into ice-water (500 mL). The organic layer is washed successively with cold 0.5N HCl (150 mL), cold water (200 mL), cold saturated solution of sodium bicarbonate (200 mL) and cold water (200 mL). The organic phase is dried over anhydrous sodium sulfate, filtered and concentrated under reduced pressure. The residue is crystallized from a mixture of ether (250 mL) and hexane (250 mL), then dried under high vacuum at 45° C. to yield methyl 1-[(S)-3-(benzyloxycarbonyl)-2-(t-BOC-amino)-propionyl]-2,3-dihydroindole-2-(S)-carboxylate, m.p. 98°–99° C.; $[\alpha]_D$=–104.40 (CHCl$_3$, c 1.1).

To a stirred solution of methyl 1-[(S)-3-(benzyloxycarbonyl)-2-(t-BOC-amino)propionyl]-2,3-dihydroindole-2-(S)-carboxylate (39 g, 80.8 mmol) in methylene chloride (300 mL) is added trifluoroacetic acid (120 mL). The solution is stirred for 1 hour, then concentrated under reduced pressure. The excess of trifluoroacetic acid is co-evaporated with toluene (200 mL) under reduced pressure. The residue is suspended in ice-cold ether (450 mL) and treated with trifluoroacetic anhydride (34.2 mL, 242 mmol). Pyridine (16.3 mL, 202 mmol) is added slowly to maintain the reaction temperature below 15° C. The mixture is stirred in an ice bath for 20 minutes, then at room temperature for 2 hours. The mixture is poured into ice-water (200 mL). The organic layer is washed successively with cold water (3×150 mL), a cold saturated solution of sodium bicarbonate (3×150 mL), water (2×100 mL) and brine (100 mL). The organic phase is dried over anhydrous sodium sulfate, filtered and concentrated under reduced pressure. The gummy residue is crystallized from a mixture of ether (150 mL) and hexane (140 mL), then dried under high vacuum at 50° C. to yield methyl 1-[(S)-3-(benzyloxycarbonyl)-2-(trifluoroacetylamino)-propionyl]-2,3-dihydroindole-2-(S)-carboxylate, m.p. 88°–90° C.; $[\alpha]_D$=–137.51 (CHCl$_3$, c 1.0).

A solution of methyl 1-[(S)-3-(benzyloxycarbonyl)-2-(trifluoroacetylamino)propionyl]-2,3-dihydroindole-2-(S)-carboxylate (30.1 g, 63 mmol) in ethyl acetate (450 mL) is hydrogenated on the Parr apparatus at 50 psi in the presence of 10% palladium on carbon (15 g) for 105 minutes. The catalyst is filtered off and the filtrate is concentrated under reduced pressure. The residue is partitioned between ether (350 mL) and water (100 mL). The organic layer is washed successively with 1N HCl (100 mL) and water (2×100 mL), then dried over anhydrous sodium sulfate and filtered. The filtrated is decolorized with charcoal, then filtered through a thin layer of silica gel (flash grade). The product is eluted with ether (200 mL). The solvent is evaporated under reduced pressure and the residue crystallized from ether-hexane (1:1). The white crystals are collected and dried under high vacuum for 1 hour at 40° C., then for 18 hours at room temperature to yield methyl 1-[(S)-3-carboxy-2-(trifluoroacetylamino)-propionyl]-2,3-dihydroindole-2-(S)-carboxylate, m.p. 157°–158° C.; $[\alpha]_D$=–188.76 (CHCl$_3$, c 1.1).

(Methyl 1-[(S)-3-carboxy-2-(trifluoroacetylamino)-propionyl]-2,3-dihydroindole-2-(S)-carboxylate) can also be prepared by the following route:

(S)-indoline 2-carboxylic acid methyl ester hydrochloride (20.0 g, 93.7 mmol) is partitioned between ethyl acetate (200 mL) and saturated NaHCO$_3$ (100 mL). After stirring, the organic layer is separated, washed successively with saturated NaHCO$_3$ (100 mL) and brine (50 mL), dried over MgSO$_4$ and filtered. To the filtrate is added dropwise over 2 hours a solution of (S)-N-trifluoroacetylaspartic anhydride (20.3 g, 103 mmol, *J. Med. Chem.* 1973, 16, 163) in ethyl acetate (100 mL). After 45 minutes of stirring, the reaction mixture is treated with 1N HCl (2×75 mL). The organic layer is washed with water (2×75 mL) then brine (75 mL), dried over MgSO$_4$ and filtered. The filtrate is concentrated in vacuo and dried under high vacuum to afford an amorphous solid consisting essentially (87%) of methyl 1-[(S)-3-carboxy-2-(trifluoroacetylamino)-propionyl]-2,3-dihydroindole-2-(S)-carboxylate. This material can be used directly in the cyclization step.

To a stirred solution of methyl 1-[(S)-3-carboxy-2-(trifluoroacetylamino)-propionyl]-2,3-dihydroindole-2-(S)-carboxylate (5 g, 12.9 mmol) in 1,2-dichloroethane (75 mL) placed under nitrogen is added dimethyl formamide (0.1 mL, 1.3 mmol) followed by oxalyl chloride (1.5 mL, 16.7 mmol). The solution is stirred for 20 minutes then cooled with an ice-bath. After 5 minutes, is added in one batch aluminum trichloride (6.9 g, 51.6 mmol). The dark amber reaction mixture is stirred at 0° C. for 5 minutes, at room temperature for 10 minutes then placed in a pre-heated oil bath (50° C.) and stirred for 16 hours under argon. An additional amount of aluminum trichloride (1.7 g, 12.9 mmol) is added and heating is continued for 3.5 hours. The mixture is cooled to room temperature then poured into ice-water (200 mL). Methylene chloride (150 mL) and water (100 mL) are added. Some insoluble material is filtered off, the organic layer is separated and the aqueous phase is extracted with methylene chloride (2×150 mL). The combined organic layers are dried over anhydrous sodium sulfate, decolorized with activated charcoal and filtered. The dark amber solution is concentrated in vacuo and the residue is treated with ether (100 mL). The insoluble material, corresponding to the epimer methyl 5- [(R)-trifluoroacetylamino]-1,2,4,5,6,7-hexahydroazepino[3,2,1-hi]indole-4,7-dione-2-(S)-carboxylate, m.p. 243° C. dec., $[\alpha]_D$=+5.31 (DMSO, c 0.9), is filtered off and the filtrate is concentrated in vacuo. The gummy residue is purified by flash chromatography on silica gel, eluting with 30% ethyl acetate in hexane. The pure fractions are concentrated and the foam is crystallized at 0° C. from ethyl acetate-hexane. The solid is dried under high vacuum at 45° C. for 1 hour to yield methyl 5-[(S)-trifluoroacetylamino]-1,2,4,5,6,7-hexahydroazepino[3,2,1-hi]indole-4,7-dione-2-(S)-carboxylate, m.p. 138°–139° C.; $[\alpha]_D$=–202.18 (DMSO, c 0.67).

Alternatively, 5-[(S)-trifluoroacetylamino]-1,2,4,5,6,7-hexahydroazepino[3,2,1-hi]-indole-4,7-dione-2-(S)-carboxylate can be obtained by epimerization of the 5-R stereomer as follows: To a stirred solution of methyl 5-[(R)-trifluoroacetylamino]-1,2,4,5,6,7-hexahydroazepino[3,2,1-hi]indole-4,7-dione-2-(S)-carboxylate (4.8 g, 12.96 mmol) in methylene chloride (100 mL) under nitrogen is added 1,8-diazabicyclo[5,4,0]undec-7-ene (DBU, 0.231 mL, 1.55 mmol). The solution is stirred for 2.5 hours, then treated with 1N HCl. The organic layer is separated, dried over anhydrous magnesium sulfate, decolorized with activated charcoal, filtered and concentrated in vacuo. The yellow foamy residue is recrystallized from ether to yield methyl 5-[(S)-trifluoroacetylamino]-1,2,4,5,6,7-hexahydroazepino[3,2,1-hi]indole-4,7-dione-2-(S)-carboxylate.

To a solution of methyl 5-[(S)-trifluoroacetylamino]-1,2,4,5,6,7-hexahydroazepino[3,2,1-hi]-indole-4,7-dione-2-(S)-carboxylate (6.31 g, 17.04 mmol) in acetic acid (100 mL) under nitrogen, is added 10% Pd-C (6.25 g). Hydrogenation is carried out in a Parr apparatus at 50 psi for 18 hours. The catalyst is filtered through Celite and washed with ethyl acetate. The filtrate is concentrated under reduced pressure. The residue is dissolved in ethyl acetate and washed with water and a cold saturated solution of sodium bicarbonate. The organic layer is dried over anhydrous magnesium sulfate, filtered and concentrated under reduced pressure to give a viscous oil that solidifies on standing. The product, methyl 5-[(S)-trifluoroacetylamino]-1,2,4,5,6,7-hexahydroazepino[3,2,1-hi]indole-4-one-2-(S)-carboxylate, can be recrystallized from ethyl acetate and hexane, m.p. 116°–117° C.; $[\alpha]_D$=–124.07 (CHCl$_3$, c 0.92).

Similarly prepared from methyl 5-[(R)-trifluoroacetylamino]-1,2,4,5,6,7-hexahydroazepino[3,2,1-hi]indole-4,7-dione-2-(S)-carboxylate is the 5R epimer, methyl 5-[(R)-trifluoroacetylamino]-1,2,4,5,6,7-hexahydroazepino[3,2,1-hi]indole-4-one-2-(S)-carboxylate, m.p. 208°–209° C.; $[\alpha]_D$=–83.29 (CHCl$_3$, c 0.95).

Alternatively, methyl 5-[(S)-trifluoroacetylamino]-1,2,4,5,6,7-hexahydroazepino[3,2,1-hi]indole-4-one-2-(S)-carboxylate, can be obtained by epimerization of the 5-R diastereomer, methyl 5-[(R)-trifluoroacetylamino]-1,2,4,5,6,7-hexahydroazepino[3,2,1-hi]-indole-4-one-2-(S)-carboxylate as follows: To a solution of methyl 5-[(R)-trifluoroacetylamino]-1,2,4,5,6,7-hexahydroazepino[3,2,1-hi]indole-4-one-2-(S)-carboxylate (1.61 g, 4.52 mmol) in dioxane (50 mL) under nitrogen is added 1,1,3,3-tetramethylguanidine (0.13 mL, 1.04 mmol). The mixture is heated at 80° C. for 5 hours. The solvent is evaporated under reduced pressure and the residue is partitioned between ethyl acetate and water. The organic layer is washed with brine, dried over anhydrous magnesium sulfate, filtered and concentrated in vacuo. Some remaining starting material (5R isomer) is crystallized from ethyl acetate-hexane and filtered off. The mother liquor, enriched in the 5S isomer is concentrated under reduced pressure. The residue is purified by flash chromatography on silica gel, eluting with 40% ethyl acetate in hexane. Concentration of the pure fractions in vacuo yields methyl 5-[(S)-trifluoroacetylamino]-1,2,4,5,6,7-hexahydroazepino[3,2,1-hi]indole-4-one-2-(S)-carboxylate.

To a stirred solution of methyl 5-[(S)-trifluoroacetylamino]-1,2,4,5,6,7-hexahydroazepino[3.2,1-hi]indole-4-one-2-(S)-carboxylate (0.985 g, 2.77 mmol) in THF (25 mL) is added a solution of lithium hydroxide (0.7 g, 16.6 mmol) in water (14 mL). The turbid mixture is stirred for 85 minutes, then quenched by addition of 2N HCl (9 mL). The solvent is co-evaporated several times under reduced pressure with a mixture of methanol (10 mL) and toluene (100 mL). The pink solid residue is dissolved in methanol (20 mL) and the solution is saturated with HCl gas. The mixture is heated to 60° C. for 1 hour, then concentrated in vacuo. The residue is treated with methylene chloride (20 mL) and an ice-cold solution of saturated sodium bicarbonate. The aqueous layer is extracted with methylene chloride (15 mL). The organic phase is dried over anhydrous magnesium sulfate, filtered and concentrated under reduced pressure. The residue is dried under high vacuum at room temperature to yield methyl 5-(S)-amino-1,2,4,5,6,7-hexahydroazepino[3,2,1-hi]indole-4-one-2-(S)-carboxylate, m.p. 96°–97° C.; $[\alpha]_D$=–251.12 (CHCl$_3$, c 0.94).

(b) Similarly prepared is methyl 5-[((S)-2-acetylthio-3-phenylpropionyl)-(R)-amino]-1,2,4,5,6,7-hexahydroazepino[3,2,1-hi]indole-4-one-2-(S)-carboxylate, from the (2-S, 5-R) diastereomer intermediate; m.p. 114°–115° C.; $[\alpha]_D$=–86.88 (CHCl$_3$, c 1).

(c) Similarly prepared is methyl 5-[((R)-2-acetylthio-3-phenylpropionyl)-(R)-amino]-1,2,4,5,6,7-hexahydroazepino[3,2,1-hi]indole-4-one-2-(S)-carboxylate, from the (2-R, 5-R) diastereomer intermediate.

(d) Similarly prepared is methyl 5-[((R)-2-acetylthio-3-phenylpropionyl)-(S)-amino]-1,2,4,5,6,7-hexahydroazepino [3,2,1-hi]indole-4-one-2-(S)-carboxylate, from the (2-R, 5-S) diastereomer intermediate; m.p. 91°–92° C.; $[\alpha]_D$=–105.68 (CHCl$_3$, c 0.69).

(e) Similarly prepared is methyl 5-[((S)-2-acetylthio-3-biphenyl-4-yl-propionyl)-(S)-amino]- 1,2,4,5,6,7-hexahydroazepino[3,2,1-hi]indole-4-one-2-(S)-carboxylate.

(f) Similarly prepared is methyl 5-[((1-acetylthio-cyclopentyl-)carbonyl)-(S)-amino]-1,2,4,5,6,7-hexahydroazepino[3,2,1-hi]indol-4-one-2-(S )-carboxylate.

EXAMPLE 2

(a) To a stirred solution of methyl 5-[((S)-2-acetylthio-3-phenylpropionyl)-(S)-amino]-1,2,4,5,6,7-hexahydroazepino [3,2,1-hi]indole-4-one-2-(S)-carboxylate (1.8 g, 3.96 mmol) in deoxygenated THF (36 mL) is added a solution of lithium hydroxide (0.64 g, 15.4 mmol) in deoxygenated water (18 mL). The yellow mixture is stirred for 45 minutes then acidified with 1N HCl (17 mL). The organic solvent is evaporated under reduced pressure, then water (20 mL) is added. The aqueous phase is extracted with methylene chloride (3×30 mL). The combined organic layers are dried over anhydrous magnesium sulfate, filtered and concentrated under reduced pressure. The residue is dissolved in methanol (12 mL) and the solution is clarified by filtration. Water (4 mL) is added and the product crystallizes upon cooling to yield 5-[((S)-2-mercapto-3-phenylpropionyl)-(S)-amino]-1,2,4,5,6,7-hexahydroazepino[3,2,1-hi]indole-4-one-2-(S)-carboxylic acid; m.p. 126°–128° C.; $[\alpha]_D$=–161.03 (CHCl$_3$, c 0.6).

(b) Similarly prepared is 5-[((S)-2-mercapto-3-phenylpropionyl)-(R)-amino]-1,2,4,5,6,7-hexahydroazepino[3,2,1-hi]indole-4-one-2-(S)-carboxylic acid, m.p. 138°–139° C.

(c) Similarly prepared is 5-[((R)-2-mercapto-3-phenylpropionyl)-(R)-amino]-1,2,4,5,6,7-hexahydroazepino[3,2,1-hi]indole-4-one-2-(S)-carboxylic acid, m.p. 141°–147° C.

(d) Similarly prepared is 5-[((R)-2-mercapto-3-phenylpropionyl)-(S)-amino]-1,2,4,5,6,7-hexahydroazepino [3,2,1-hi]indole-4-one-2-(S)-carboxylic acid; m.p. 200°–202° C.; $[\alpha]_D$=–165.83 (CHCl$_3$, c 0.55).

(e) Similarly prepared is 5-[((S)-2-mercapto-3-biphenyl-4-yl-propionyl)-(S)-amino]-1,2,4,5,6,7-hexahydroazepino [3,2,1-hi]indole-4-one-2-(S)-carboxylic acid, m.p. 130°–138° C.; $[\alpha]_D$=–124.04 (CH$_2$Cl$_2$, c 0.81).

(f) Similaraly prepared is 5-[((1-mercapto-cyclopentyl)-carbonyl)-(S)-amino]-1,2,4,5,6,7-hexahydroazepino[3,2,1-hi]indole-4-one-2-(S)-carboxylic acid, m.p. 186°–187° C.; $[\alpha]_D$=–137.12 (CHCl$_3$, c 0.77).

EXAMPLE 3

(a) To a stirred solution of cobalt dichloride (31 mg, 0.24 mmol) in acetonitrile (5 mL) and methylene chloride (1 mL) under nitrogen is added acetic anhydride (0.34 mL, 3.6 mmol), followed by a solution of 5-[((S)-2-mercapto-3-phenylpropionyl)-(S)-amino]-1,2,4,5,6,7-hexahydroazepino [3,2,1-hi]indole-4-one-2-(S)-carboxylic acid (497 mg, 1.21 mmol) (reaction according to Tetrahedron Letters, 1986, 3791). After 1 hour of reaction at room temperature, the mixture is heated at 50° C. for 3 hours. The solvent is evaporated in vacuo and the residue is dissolved in ethyl acetate (30 mL) then washed with water (3×10 mL). The organic layer is dried over anhydrous sodium sulfate, then filtered and concentrated under reduced pressure. The residue is purified by flash chromatography on silica gel, eluting with 40% ethyl acetate in hexane containing 3% of acetic acid. The product is recrystallized from ether-hexane and dried at 50° C. under high vacuum to yield 5-[((S)-2-acetylthio-3-phenylpropionyl)-(S)-amino]-1,2,4,5,6,7-hexahydroazepino[3,2,1-hi]indole-4-one-2-(S)-carboxylic acid; m.p. 93°–102° C.; $[\alpha]_D$=–160.27 (CHCl$_3$, c 1.5).

(b) Similarly prepared is 5-[((S)-2-(2,2-dimethyl-propionylthio)-3-phenylpropionyl)-(S)-amino]-1,2,4,5,6,7-hexahydroazepino[3,2,1-hi]indole-4-one-2-(S)-carboxylic acid; m.p. 105°–110° C.; $[\alpha]_D$=–159.73 (CHCl$_3$, c 0.8).

EXAMPLE 4

(a) To a stirred solution of cobalt dichloride (15 mg, 0.1 mmol) in acetonitrile (2.5 mL) under nitrogen is added a solution of 5-[((S)-2-mercapto-3-phenylpropionyl)-(S)-amino]-1,2,4,5,6,7-hexahydroazepino[3,2,1-hi]indole-4-one-2-(S)-carboxylic acid (240 mg, 0.58 mmol) and benzoyl chloride (0.75 mL, 0.64 mmol) in acetonitrile (2.5 mL) (reaction according to Tetrahedron Letters, 1986, 3791). After 1 hour of reaction at room temperature, the mixture is heated at 55° C. for 45 minutes, then stirred at room temperature for 3 days. The solvent is evaporated in vacuo and the residue is dissolved in ethyl acetate (20 mL), then washed with water (3×10 mL). The organic layer is dried over anhydrous sodium sulfate then filtered and concentrated under reduced pressure. The residue is purified by flash chromatography on silica gel, eluting with 50% ethyl acetate in hexane containing 2% of acetic acid. The pure fractions are co-evaporated several times with toluene. The product, 5-[((S)-2-benzoylthio-3-phenylpropionyl)-(S)-amino]-1,2,4,5,6,7-hexahydroazepino[3,2,1-hi]indole-4-one-2-(S)-carboxylic acid, is obtained as an amorphous solid; m.p. 85°–90° C.; $[\alpha]_D$=–168.95 (CHCl$_3$, c 2.1).

(b) Similarly prepared is 5-[((S)-2-(thiophene-2-carbonylthio)-3-phenylpropionyl)-(S)-amino]-1,2,4,5,6,7-hexahydroazepino[3,2,1-hi]indole-4-one-2-(S)-carboxylic acid; m.p. 110°–125° C.; $[\alpha]_D$=–187.22 (CHCl$_3$, c 0.6).

c) Similarly prepared using methoxyacetyl chloride is 5-[((S)-2-methoxyacetylthio-3-phenylpropionyl)-(S)-amino]-1,2,4,5,6,7-hexahydroazepino[3,2,1-hi]indole-4-one-2-(S)-carboxylic acid; amorphous solid, m.p. 84°–89° C.; $[\alpha]_D$=–164.21 (CHCl$_3$, c 0.98).

(d) Similarly prepared using nicotinoyl chloride hydrochloride is 5-[((S)-2-nicotinoylthio-3-phenylpropionyl)-(S)-amino]-1,2,4,5,6,7-hexahydroazepino[3,2,1-hi]-indole-4-one-2-(S)-carboxylic acid; m.p. 126°–140° C. dec.; $[\alpha]_D$=–201.69 (MeOH, c 0.83).

(e) Similarly prepared using 4-morpholinoacetyl chloride hydrochloride is 5-[((S)-2-(4-morpholino)-acetylthio-3-phenylpropionyl)-(S)-amino]-1,2,4,5,6,7-hexahydroazepino[3,2,1-hi]indole-4-one-2-(S)-carboxylic acid; m.p. 98°–106° C.

EXAMPLE 5

Similarly to the procedures described in examples 1 and 2, the following compounds are prepared from the corresponding co-substituted thioacetic acid.

(a) 5-[((S)-2-mercapto-3-methylbutanoyl)-(S)-amino]-1,2,4,5,6,7-hexahydro-azepino[3,2,1-hi]indole-4-one-2-(S)-carboxylic acid, m.p. 88°–119° C.; $[\alpha]_D$=–180.52 (CHCl$_3$, c 0.78);

(b) 5-[((S)-2-mercapto-3-(R)-methylpentanoyl)-(S)-amino]-1,2,4,5,6,7-hexahydro-azepino[3,2,1-hi]indole-4-one-2-(S)-carboxylic acid, m.p. 84°–87° C.;

(c) 5-[((S)-2-mercapto-2-cyclohexylacetyl)-(S)-amino]-1,2,4,5,6,7-hexahydro-azepino[3,2,1-hi]indole-4-one-2-(S)-carboxylic acid, m.p. 183°–185° C.; $[\alpha]_D$=–178.25 (CHCl$_3$, c 0.70);

(d) 5-[((S)-2-mercapto-3-cyclohexylpropionyl)-(S)-amino]-1,2,4,5,6,7-hexahydro-azepino[3,2,1-hi]indole-4-one-2-(S)-carboxylic acid;

(e) 5-[((S)-2-mercapto-3-(4-hydroxyphenyl)propionyl)-(S)-amino]-1,2,4,5,6,7-hexahydro-azepino[3,2,1-hi]indole-4-one-2-(S)-carboxylic acid.

EXAMPLE 6

Similarly to the procedures described in examples 1 and 2, the following compounds are prepared:

(a) 5-[((R)-2-(biphenyl-4-ylmethyl)-3-mercapto-propionyl)-(S)-amino]-1,2,4,5,6,7-hexahydroazepino[3,2,1-hi]indole-4-one-2-(S)-carboxylic acid, m.p. 163°–165° C.; $[\alpha]_D$=–216.89 (CHCl$_3$, c 0.94), starting from α-(biphenyl-4-ylmethyl)-β-(acetylthio) propionic acid;

(b) 5-[((S)-2-biphenyl-4-ylmethyl-3-mercapto-propionyl)-(S)-amino]-1,2,4,5,6,7-hexahydroazepino[3,2,1-hi]indole-4-one-2-(S)-carboxylic acid, m.p. 189°–190° C.; $[\alpha]_D$=–45.52 (CHCl$_3$, c 0.92), starting from α-(biphenyl-4-ylmethyl)-β-(acetylthio) propionic acid;

(c) 5-[((S)-2-benzyl-3-mercapto-propionyl)-(S)-amino]-1,2,4,5,6,7-hexahydro-azepino[3,2,1-hi]indole-4-one-2-(S)-carboxylic acid, starting from α-benzyl-β-(acetylthio) propionic acid;

(d) 5-[((S)-2-trifluorometyl-3-mercapto-propionyl)-(S)-amino]-1,2,4,5,6,7-hexahydroazepino[3,2,1-hi]indole-4-one-2-(S)-carboxylic acid, starting from α-trifluoromethyl-β-(acetylthio) propionic acid.

EXAMPLE 7

Similarly to procedures in examples 1 and 2 are prepared the following compounds.

(a) 5-[((S)-2-mercapto-3-phenylpropionyl)-(S)-amino]-1,2,4,5,6,7-hexahydro-azepino[3,2,1-hi]indole-4,7-dione-2-(S)-carboxylic acid starting with methyl 5-[(S)-trifluoroacetylamino]-1,2,4,5,6,7-hexahydroazepino [3,2,1-hi]indole-4,7-dione-2-(S)-carboxylate (see example 1) and converting such to the 5-amino starting material by removal of trifluoroacetyl group according to the procedure previously described.

(b) Similarly prepared is 5-[((S)-2-mercapto-3-phenylpropionyl)-(S)-amino]-7-(R)-hydroxy-1,2,4,5,6,7-hexahydro-azepino[3,2,1-hi]indole-4-one-2-(S)-carboxylic acid, m.p. 208°–209° C. starting from methyl 5-[((S)-trifluoroacetylamino)-7-(R)-hydroxy-1,2,4,5,6,7-hexahydroazepino[3,2,1-hi]indole-4-one-2-(S)-carboxylate which is prepared as follows:

To a solution of methyl 5-[((S)-trifluoroacetylamino)-1,2,4,5,6,7-hexahydroazepino [3,2,1-hi]indole-4,7-dione-2-(S)-carboxylate (see example 1) in ethyl acetate under nitrogen, is added 10% Pd-C. Hydrogenation is carried out at atmospheric pressure for 8 hours. The catalyst is filtered through Celite and washed with ethyl acetate. The filtrate is concentrated under reduced pressure. The residue is dissolved in ethyl acetate and washed with water and a cold saturated solution of sodium bicarbonate. The organic layer is dried over anhydrous magnesium sulfate, filtered and concentrated under reduced pressure. The product is separated by flash-chromatography on silica gel, eluting with a gradient of ethyl acetate in hexane (10 to 30%) to give the 7-hydroxy-5-trifluoroacetylamino compound. Such is then converted to the 5-amino starting material according to procedure described in example 1.

EXAMPLE 8

(a) Methyl 6-[((S)-2-acetylthio-3-phenyl-propionyl)-(S)-amino]-2,3,5,6,7,8-hexahydro-1H-pyrido[3,2,1-jk][1]-benzazepin-5-one-3(S)-carboxylate can be prepared similarly to the previous examples using as starting material (S)-tetrahydroquinoline-2-carboxylic acid methyl ester instead of (S)-indoline-2-carboxylic acid methyl ester. The structure is:

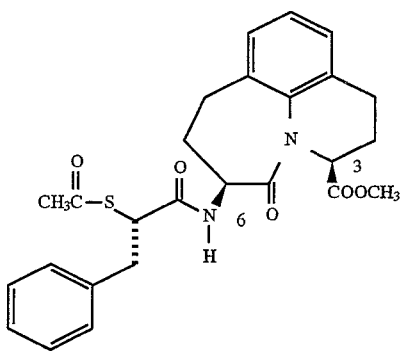

(b) Hydrolysis gives 6-[((S)-2-mercapto-3-phenylpropionyl)-(S)-amino]-2,3,5,6,7,8-1H-pyrido[3,2,1-jk][1]-benzazepin-5-one-3(S)-carboxylic acid.

EXAMPLE 9

Preparation of 3000 capsules each containing 25 mg of the active ingredient, for example 5-[((S)-2-mercapto-3-phenylpropionyl)-(S)-amino]-1,2,4,5,6,7-hexahydroazepino[3,2,1-hi]indole-4-one-2-(S)-carboxylic acid.

Active ingredient 75.00 g

Lactose 750.00 g

Microcrystalline cellulose 300.00 g

Polyvinylpyrrolidone 30.00 g

Purified water q.s.

Magnesium stearate 9.0 g

The active ingredient is passed through a No. 30 hand screen.

The active ingredient, lactose, cellulose and polyvinylpyrrolidone are blended for 15 minutes in a mixer. The blend is granulated with sufficient water (about 500 mL), dried in an oven at 35° C. overnight, and passed through a No. 20 screen.

Magnesium stearate is passed through a No. 20 screen, added to the granulation mixture, and the mixture is blended for 5 minutes in a mixer. The blend is encapsulated in No. 0 hard gelatin capsules each containing an amount of the blend equivalent to 25 mg of the active ingredient.

What is claimed is:

1. A compound of the formula

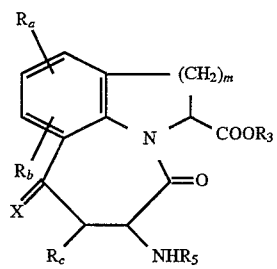

wherein

X represents oxo;

$R_a$ and $R_b$ independently represent hydrogen, hydroxy, lower alkoxy, nitro, amino, or halogen; or $R_a$ and $R_b$ on adjacent carbon atoms taken together represent lower alkylenedioxy;

$R_c$ represents hydrogen, lower alkyl or aryl-lower alkyl;

m represents one or two;

$R_5$ is an amino protecting group or hydrogen;

$COOR_3$ represents carboxyl or carboxyl derivatized in form of a pharmaceutically acceptable ester, or a salt thereof.

2. A compound according to claim 1 wherein $R_c$ represents hydrogen.

3. A compound according to claim 1 wherein m is one.

4. A compound according to claim 1 wherein m is two.

5. A compound according to claim 1 which is the S,S-isomer of the formula

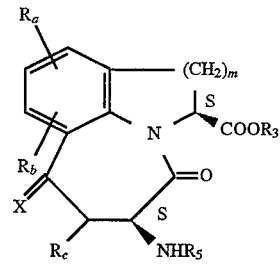

wherein X, $R_a$, $R_b$, $R_c$, $R_5$, m, n and $COOR_3$ have the meanings as defined in said claim; or a pharmaceutically acceptable salt thereof.

6. A compound according to claim 5 wherein m is one.

7. A compound according to claim 5 wherein m is one; $R_a$, $R_b$, $R_c$, and $R_5$ represent hydrogen; and $COOR_3$ represents esterified carboxyl.

8. A compound according to claim 5 wherein m is two; $R_a$, $R_b$, $R_c$ and $R_5$ represent hydrogen; and $COOR_3$ represents esterified carboxyl.

9. A compound according to claim 5 which is methyl 5-[(S)-trifluoroacetylamino]-1,2,4,5,6,7-hexahydroazepino[3,2,1-hi]indole-4,7-dione-2-(S)-carboxylate.

10. A process for the preparation of a compound of the formula

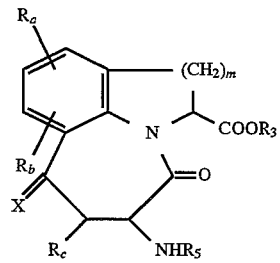

wherein

X represents oxo, one hydrogen or lower alkoxy and one hydrogen, or two hydrogens;

$R_a$ and $R_b$ independently represent hydrogen, hydroxy, lower alkoxy, nitro, amino or halogen; or $R_a$ and $R_b$ on adjacent carbon atoms taken together represent lower alkylenedioxy;

$R_c$ represents hydrogen, lower alkyl or aryl-lower alkyl;

m represents one or two;

$R_5$ represents hydrogen or an amino protecting group;

COOR₃ represents carboxyl or carboxyl derivatized in form of a pharmaceutically acceptable ester; or a salt thereof; which comprises cyclizing a reactive functional derivative of formula

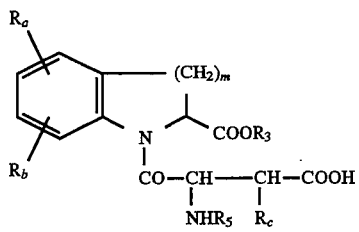

wherein $R_5$ represents an amino protecting group, under Friedel-Crafts acylation conditions; and, if desired, converting a resulting compound, wherein X represents oxo, into a compound, wherein X represents one hydrogen and one hydroxy; or, if desired, converting a resulting compound, wherein X represents oxo, into a compound, wherein X represents two hydrogens; then, if desired, removing said protecting group $R_5$, and then isolating the resulting compound wherein $R_5$ is hydrogen.

11. A process according to claim 10 for the preparation of a compound wherein m is one and $R_c$ represents hydrogen.

12. A process according to claim 10 for the preparation of methyl 5-(S)-amino-1,2,4,5,6,7-hexahydroazepino[3,2,1-hi]indol-4-one-2-(S)-carboxylate.

* * * * *